(12) United States Patent
Davies et al.

(10) Patent No.: US 6,297,225 B1
(45) Date of Patent: Oct. 2, 2001

(54) TREATMENT OF HIGHLY VASCULAR TUMORS

(75) Inventors: Donald Davies, Beaconsfield; Robert John Edwards, Radlett; Nigel John Gooderham, Windlesham; Sunil Shaunak, Hertfordshire, all of (GB)

(73) Assignee: M L Laboratories PLC, Liverpool (GB)

( * ) Notice: Subject to any disclaimer, the term of this patent is extended or adjusted under 35 U.S.C. 154(b) by 0 days.

(21) Appl. No.: 09/319,483

(22) PCT Filed: Dec. 1, 1997

(86) PCT No.: PCT/GB97/03315

§ 371 Date: Sep. 22, 1999

§ 102(e) Date: Sep. 22, 1999

(87) PCT Pub. No.: WO98/24421

PCT Pub. Date: Jun. 11, 1998

(30) Foreign Application Priority Data

Dec. 4, 1996 (GB) .................................................. 9625193

(51) Int. Cl.$^7$ .................................................. A61K 31/70
(52) U.S. Cl. .............................................. 514/58; 514/60
(58) Field of Search .......................................... 514/58, 60

(56) References Cited

U.S. PATENT DOCUMENTS 5,439,892 * 8/1995 Davies .................................... 514/58

FOREIGN PATENT DOCUMENTS

WO 89/05646   6/1989   (WO) .
WO 95/34313   12/1995  (WO) .

OTHER PUBLICATIONS

The Merck Manual of Diagnosis & Therapy 16$^{th}$ ed. (1992) p. 2460 "Kaposi'sarcoma".

* cited by examiner

*Primary Examiner*—Elli Peselev
(74) *Attorney, Agent, or Firm*—Garvey, Smith, Nehrbass & Doody, L.L.C.

(57) ABSTRACT

A method of treating a patient having a highly vascular tumor includes administering a therapeutically effective amount of dextrin sulphate to the patient. The highly vascular tumor can be, for example, Kaposi's sarcoma. The treatment results in regression of the tumors and the improvement persists for a considerable time after completion of the treatment.

14 Claims, No Drawings

TREATMENT OF HIGHLY VASCULAR TUMORS

This invention relates to the treatment of patients suffering from highly vascular tumours. Such tumours have extensive new formation of well formed and poorly formed blood vessels, with numerous capillaries and larger channels which are composed mainly of a layer of endothelium supported by cells of different types (e.g. small spindle cells, plasma cells, lymphocytes) which can in themselves be abnormal.

The invention is particularly concerned with a condition known as Kaposi's Sarcoma. A sarcoma is a malignant tumour of connective tissue of mesenchymal origin. The condition known as Kaposi's Sarcoma (KS) is a multifocal, reactive, vascular proliferation which can, in time, acquire some of the features associated with a malignant tumour. KS is usually seen in immunosuppressed patients and occurs in several distinct clinical forms, which include:

(i) Sporadic (classic) KS. This was the first form of KS to be observed. It was seen many years ago (by Kaposi) in Jewish communities in Eastern Europe.

(ii) Endemic (African) KS. This occurs in sub-Saharan Africa.

(III) Epidemic (AIDS) KS. This occurs in AIDS patients.

(iv) Iatrogenic KS. This occurs mainly in transplant patients who have been given immunosuppressive medication.

As yet, it has not been possible to establish clear biological or histopathological differences which would serve to explain these different clinical and pathological forms of KS.

The evolution of both skin and lymphadenopathic KS from early angiomatous lesions to the patch and nodular stages of KS is characterised by a progressive increase in the number of spindle cells. The highly vascular nature of this tumour may suggest that it develops from aberrant lymphatico-venous connections which, in early macular lesions, are lined by cells which are phenotypically similar to lymphatic epithelium. However, questions remain about the histocytogenic origin of the spindle cells and the pathogenic factors which drive the proliferation of these cells during the evolution of KS. These questions revolve around whether the KS lesion constitutes clonal malignant proliferation or a hyperproliferative "reactive" response to an unknown stimulus or stimuli. It is possible that the mixed cell proliferation is produced by a minority of tumour cells which have constitutive genetic abnormalities or aneuploidy.

The heterogeneity of proliferating cells in a KS lesion suggests a complex network of cell stimulation. In the case of KS-derived spindle cells which have been cultured in vitro, several cytokines with autocrine and paracrine growth properties (e.g. beta-FGF, IL-1, GM-CSF, platelet derived growth factor, and oncostatin-M) have been shown to induce local angiogenesis in the skin of nude mice and in a chorioallantoic membrane assay.

In the current clinical approaches to the treatment of KS it has been found that early skin lesions respond to radiotherapy. More severe, disseminated disease requires treatment with cytotoxic chemotherapeutic agents such as doxorubicin, vincristine and bleomycin which have to be administered intravenously. These treatment regimens are often associated with severe clinical toxicity in patients who are already debilitated and immunosuppressed. One of the most common reasons for interrupting cycles of chemotherapy during a course of treatment of KS with anthracycline drugs (e.g. adriamycin) is neutropenia. More recently, administration of liposomal preparations of daunorubicin and doxorubicin has also resulted in the rapid regression of KS lesions. For those KS lesions which are seen in patients on iatrogenic immunosuppression the tumour regresses when the degree of immunosuppression is reduced.

The number of cases of AIDS-related cases of KS has increased dramatically in recent years. It has been postulated that KS spindle cell growth in vitro and in vivo may be modulated by HIV-1. However, both immunohistochemistry for HIV-1 proteins as well as PCR for HIV-1 DNA have failed to find any evidence that HIV-1 is present in the spindle cell population of epidemic KS lesions. Moreover, treatment of KS lesions with drugs known to reduce the viral load of HIV-1 in the blood substantially, such as zidovudine (AZT), didanosine (ddI) and/or zalcitabine (ddC), does not result in the regression or the healing of KS lesions. Thus, it seems that KS is not caused simply by the presence of HIV-1, particularly since KS can appear in patients who display no sign of this virus. Evidently, therefore, the fact that a drug is known to have anti-HIV activity is not an indication that it is of value for the treatment of KS.

We have found that administration of dextrin sulphate to patients having highly vascular tumours, in particular KS lesions, results in regression of the tumours.

The present invention provides a method of treatment of a patient having a highly vascular tumour, especially KS, which comprises administering dextrin sulphate to the patient.

Dextrin sulphates are known compounds. They are produced by sulphation of dextrins, which are mixtures of glucose polymers produced by hydrolysis of starch. These glucose polymers have a wide range of polymerisation. The degree of polymerisation (D.P.) varies from 1 (the monomer, glucose) up to very high values, for example up to a hundred thousand or more glucose units.

Typically, the direct result of hydrolysing a starch is a dextrin containing a high proportion of polymers of relatively low molecular weight and might for example contain up to 60% by weight of glucose polymers of D.P. less than 12. The dextrin sulphates used in the present invention can have a wide range of composition, but are preferably derived from dextrins containing at least 50% by weight, preferably more than 90%, of glucose polymers greater than 12, and/or containing less than 10%, preferably less than 5%, by weight of glucose polymers of D.P. less than 12. The weight average molecular weight of the dextrin may, for example, be from 10,000 to 35,000, preferably 15,0000 to 25,000. (The technique used to determine the molecular weight of the dextrin is high-pressure liquid chromatography using chromatographic columns calibrated with dextran standards, as designated by Alsop et al., J. Chromatography 246, 227–240, 1989). Preferably, the dextrin contains not more than 10%, preferably less than 5%, by weight of polymers of molecular weight greater than 40,000. The desired weight average molecular weight and polymer profile is achieved by subjecting a dextrin to fractionation, using known techniques, including solvent precipitation and membrane fractionation. Among the dextrins from which the dextrin sulphates suitable for use in the present invention can be derived are those described in European patent specifications Nos. 115911, 153164, and 207676.

Dextrin sulphates have been previously used pharmaceutically. For exanple, British patent specification 871,590 discloses the use of certain dextrin sulphates as antilipaemic agents, and U.S. Pat. No. 5,439,892 the use of certain dextrin sulphates as anti-HIV agents. These references also describe processes for the production of dextrin sulphates; their disclosures are incorporated herein by reference.

The Scandinavian Journal of Immunology, Volume 29 (2) pp 181–92, 1989 discloses tumour regression after treatment with aminated β1-3D polyglucose.

In the method of the invention the dextrin sulphate can be administered to the patient by any route, enteral or parenteral, at the discretion of the clinician. Intraperitoneal administration is particularly effective, but the dextrin sulphate can, for example, also be given orally, intravenously, or can be directly injected into the lesions of the tumour on a lesion by lesion basis, or can be topically applied. The dosage level is to be determined by the clinician.

Dextrins can be sulphated in the 2, 3, and 6 positions, and a fully sulphated dextrin therefore contains three sulphate groups per glucose unit. The dextrin sulphate used in the present invention may have any degree of sulphation, but preferably it contains at most two, more preferably from 0.5 to 1.5, sulphate groups per glucose unit. Also, the dextrin sulphate is preferably dextrin-2-sulphate, dextrin-6-sulphate or a mixture thereof.

The following example is given by way of illustration or the invention.

EXAMPLE

A composition for use in administering dextrin sulphate intraperitoneally was prepared, in the form of a sterile aqueous solution containing:

| | |
|---|---|
| Dextrin sulphate | 100 micrograms/ml |
| Glucose polymer mixture | 10 grams/liter |
| Na | 132 mmol/liter |
| Ca | 1.75 mmol/liter |
| Mg | 0.75 mmol/liter |
| Lactate | 35 mmol/liter |

The dextrin sulphate was dextrin-2-sulphate, prepared as described in Example 3 of U.S. Pat. No. 5,439,892. The glucose polymer mixture, present in the solution as an osmotic agent, was the glucose polymer mixture described in Example 2 of European specification 153164; it contained 91.9% of polymers of D.P. greater than 12 and 7.9% of polymers of from D.P. 2 to 10, and had a weight average molecular weight of 23,700.

The above solution was administered intraperitoneally to three patients with multifocal, widely disseminated KS and having late stage AIDS. 1.5 liters of the solution was introduced daily into the peritoneal cavity of the patient by way of indwelling catheter. The solution was allowed to remain in the peritoneal cavity for twenty-four hours and then replaced by fresh solution. This treatment was continued for thirty days.

Regression of KS Lesions was observed. This response to the treatment was seen both on the skin and for those lesions which were on mucous membranes (i.e. within the mouth). The response was slow and occurred over a period of months even though the period of treatment was only 30 days. The improvement in the condition of the patient, who did not receive further treatment, persisted for a considerable time.

There are, as yet, no formally accepted staging criteria for KS. However, the improvement in the patient's condition was assessed in accordance with guidelines issued by the AIDS Clinical Trials Group Oncology Committee, which suggests the following criteria:

(a) Nodular lesions become flat.
(b) Lesions become darker in colour (i.e. mauve).
(c) The epithelium desquamates.
(d) Tumour-associated oedema resolves.
(e) Lymphoedema resolves
(f) Healed lesions develop a brown/tan halo.
(g) Previously ulcerated areas of large KS lesions which are not amenable to any other form of current therapy have healed.

In the case of the three patients treated as described above the process of healing was slow and took months rather than weeks. During the latter phase of the healing process of lesions which were present before the start of administration of dextrin sulphate, some new lesions were seen to arise. They were however morphologically quite distinct from those seen before the treatment in that they were very small (being measurable in millimeters rather than in centimeters), pink, and flat. Also, they grew very slowly and were sometimes associated with a small number of satellite lesions. This is a very unusual presentation of KS in patients with late stage AIDS.

In the above Example the dextrin sulphate was given to the patients in a carrier solution which was removed from the peritoneal cavity of the patients and replaced by fresh solution on a daily basis. Other treatment regimens, also using intraperitoneal administration are feasible. if the carrier solution is left within the peritoneal cavity, and not removed therefrom, it is cleared by the body from the peritoneal cavity, mainly into the lymphatic circulation. Full clearance is usually effected in about forty-eight hours. Accordingly it is possible to use treatment regimens in which the step of removing carrier liquid from the patient is omitted; for example, (a) the dextrin sulphate may be administered daily in a volume of carrier liquid comparable with the daily clearance volume, or (b) the dextrin sulphate may be given to the patient less often than daily, perhaps two or three times a week, depending on the clearance rate.

As the aetiology and pathogenesis of KS is not understood, the mechanism of action of dextrin sulphate on KS lesions is not yet known. The ideal treatment regimen therefore still remains to be determined and may of course vary from patient to patient. However, as is evident from the above Example, the dextrin sulphate does not have to be present continuously for the KS to show improvement. It may therefore be appropriate for some patients to be given dextrin sulphate less frequently than on a daily basis, perhaps once a week.

What is claimed is:

1. A method of treating a patient having a highly vascular tumour which comprises administering a therapeutically effective amount of dextrin sulphate to the patient.

2. The method of claim 1 wherein said highly vascular tumour is Kaposi's sarcoma.

3. The method of claim 1 wherein the dextrin sulphate is administered to the patient intraperitoneally.

4. The method of claim 1 wherein the dextrin sulphate is derived from a dextrin having at least 50% by weight of glucose polymers of D.P. greater than 12.

5. The method of claim 1 wherein the dextrin sulphate is derived from a dextrin having more than 90% by weight of glucose polymers of D.P. greater than 12.

6. The method of claim 1 wherein the dextrin sulphate is derived from a dextrin containing less than 10% by weight of glucose polymers of D.P. less than 12.

7. The method of claim 1 wherein the dextrin sulphate is derived from a dextrin containing less than 5% by weight of glucose polymers of D.P. less than 12.

8. The method of claim 1 wherein the dextrin sulphate is derived from a dextrin having a weight average molecular weight of from 10,000 to 35,000.

9. The method of claim 1 wherein the dextrin sulphate is derived from a dextrin containing less than 10% by weight of glucose polymers of molecular weight greater than 40,000.

10. The method of claim 1 wherein the dextrin sulphate is derived from a dextrin containing less than 5% by weight of glucose polymers of molecular weight greater than 40,000.

11. The method of claim 1 wherein the dextrin sulphate contains at most two sulphate groups per glucose unit.

12. The method of claim 1 wherein the dextrin sulphate contains between 0.5 and 1.5 sulphate groups per glucose unit.

13. The method of claim 1 wherein the dextrin sulphate is dextrin-2-sulphate or dextrin-6-sulphate or a mixture thereof.

14. The method of claim 1 wherein the dextrin sulphate is derived from a dextrin having a weight average molecular weight of from 15,000 to 25,000.

* * * * *